(12) United States Patent
Secondini

(10) Patent No.: US 11,998,554 B2
(45) Date of Patent: Jun. 4, 2024

(54) COMPOSITION COMPRISING LIPOIC ACID AND VITAMIN D FOR THE PREVENTION AND THE TREATMENT OF NEURODEGENERATIVE DISEASES AND PERIPHERAL NEUROPATHIES

(71) Applicant: URIACH ITALY S.R.L., Assago (IT)

(72) Inventor: Lorenzo Secondini, Assago (IT)

(73) Assignee: URIACH ITALY S.R.L., Assago (IT)

( * ) Notice: Subject to any disclaimer, the term of this patent is extended or adjusted under 35 U.S.C. 154(b) by 362 days.

(21) Appl. No.: 17/272,623

(22) PCT Filed: Sep. 10, 2019

(86) PCT No.: PCT/IB2019/057612
§ 371 (c)(1),
(2) Date: Mar. 1, 2021

(87) PCT Pub. No.: WO2020/053754
PCT Pub. Date: Mar. 19, 2020

(65) Prior Publication Data
US 2022/0211724 A1    Jul. 7, 2022

(30) Foreign Application Priority Data

Sep. 10, 2018 (IT) .................. 102018000008450

(51) Int. Cl.
*A61K 31/593* (2006.01)
*A61K 31/385* (2006.01)

(52) U.S. Cl.
CPC .......... *A61K 31/593* (2013.01); *A61K 31/385* (2013.01)

(58) Field of Classification Search
CPC .... A61K 31/55; A61K 31/132; A61K 31/198; A61K 31/396; A61K 31/426; A61K 31/433; A61K 31/44; A61K 31/485; A61K 31/506; A61K 45/06; A61K 31/4035; A61K 31/4245; A61K 31/428; A61K 31/4453; A61K 31/635; A61P 9/10
See application file for complete search history.

(56) References Cited

U.S. PATENT DOCUMENTS

| | | | |
|---|---|---|---|
| 6,365,622 B1 * | 4/2002 | Cavazza | A61P 25/02 514/556 |
| 2008/0038367 A1 | 2/2008 | Saloum | |
| 2008/0187526 A1 | 8/2008 | Prasad et al. | |
| 2010/0331286 A1 | 12/2010 | Chow | |
| 2011/0052567 A1 * | 3/2011 | Petkovich | A61K 31/00 435/6.14 |
| 2015/0139972 A1 * | 5/2015 | Haase | A61K 33/00 424/94.1 |
| 2018/0055802 A1 | 3/2018 | Mastaloudis et al. | |

FOREIGN PATENT DOCUMENTS

| | | |
|---|---|---|
| WO | WO 2010/002093 A1 | 1/2010 |
| WO | WO 2019/197967 A1 | 10/2019 |

OTHER PUBLICATIONS

Erbas et al. Cholecalciferol (vitamin D3) improves cognitive dysfunction and reduces inflammation in a rat fatty liver model of metabolic syndrome. Life Sciences 103 (2014) 68-72. (Year: 2014).*
NIH National Cancer Institute. Oxidative Stress. Retrieved from the internet on May 5, 2023, https://www.cancer.gov/publications/dictionaries/cancer-terms/def/oxidative-stress. (Year: 2023).*
NIH National Cancer Institute. Antioxidant. Retrieved from the internet on May 5, 2023, https://www.cancer.gov/search/results?swKeyword=antioxidant (Year: 2023).*
ConvertUnits. Convert nanomolar to micromolar. Retrieved from the internet on Aug. 14, 2023, https://www.convertunits.com/from/nanomolar/to/micromolar. (Year: 2023).*
Jana et al., "Astrocytes, Oligodendrocytes and Schwann Cells" In: Ikezu, T., Gendelman, H. (eds) Neuroimmune Pharmacology, Springer International Publishing Switzerland, 2017, pp. 117-125.
Basit et al., "Vitamin D for the treatment of painful diabetic neuropathy", BMJ Open Diabetes Research and Care, 2016, 4: e000148.
Database WPI, Week 201007, Thomson Scientific, AN 2010-A36579, XP002791097, 2010.
Database WPI, Week 201349, Thomson Scientific, AN 2013-K35772, XP002796002, 2013.
Hesselink et al., "An integrative medicine approach for the treatment of neuropathic pain", European Journal of Integrative Medicine, Elsevier, 2010, 2(4): 190.
Molinari et al., "Role of Combined Lipoic Acid and Vitamin D3 on Astrocytes as a Way to Prevent Brain Ageing by Induced Oxidative Stress and Iron Accumulation", Oxidative Medicine and Cellular Longevity, 2019, 2019:1-16.
Molz et al., "Potential Therapeutic Effects of Lipoic Acid on Memory Deficits Related to Aging and Neurodegeneration", Frontiers in Pharmacology, 2017, 8:849.
Uberti et al., "Protective effects of 1 [alpha], 25-Dihydroxyvitamin D3 on cultured neural cells exposed to catalytic iron", Physiological Reports, 2016, 4(11): e12769.

* cited by examiner

*Primary Examiner* — Amy C Bonaparte
*Assistant Examiner* — Lauren Wells
(74) *Attorney, Agent, or Firm* — James S. Keddie; Bozicevic, Field & Francis LLP

(57) ABSTRACT

The present invention regards a composition comprising lipoic acid, or an acceptable pharmaceutical or food grade salt thereof or a derivative thereof, and a vitamin D, preferably vitamin D3 and/or vitamin D2, for use in a method for the treatment of neurodegenerative diseases and/or for the treatment of peripheral neuropathies.

6 Claims, 8 Drawing Sheets

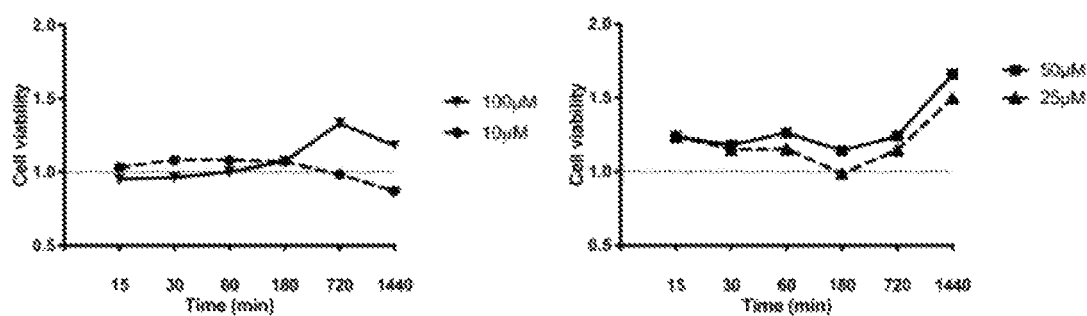
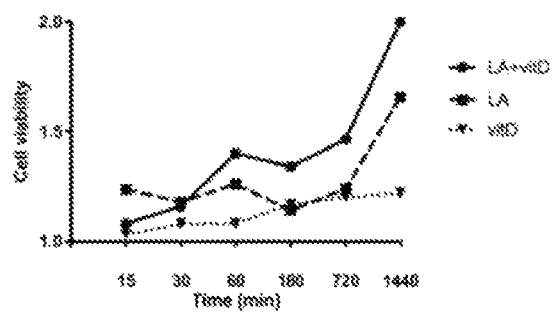
Figure 1(a). Cell viability measured in dose-response and time-dependent studies of LA in astrocytes
Figure 1(b). Cell viability measured in time-dependent studies of vitD, LA and LA+vitD combination in astrocytes.

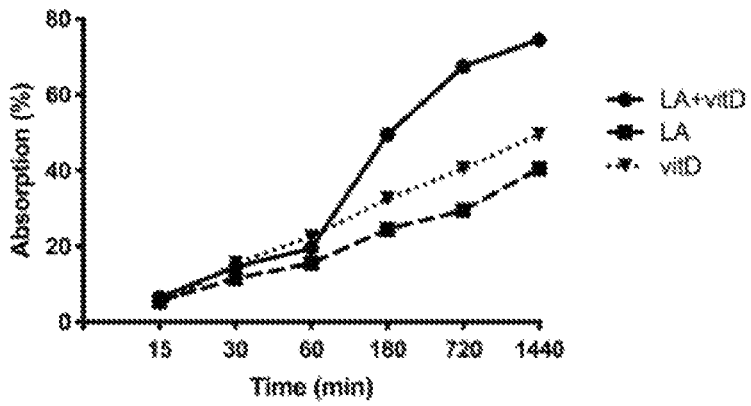
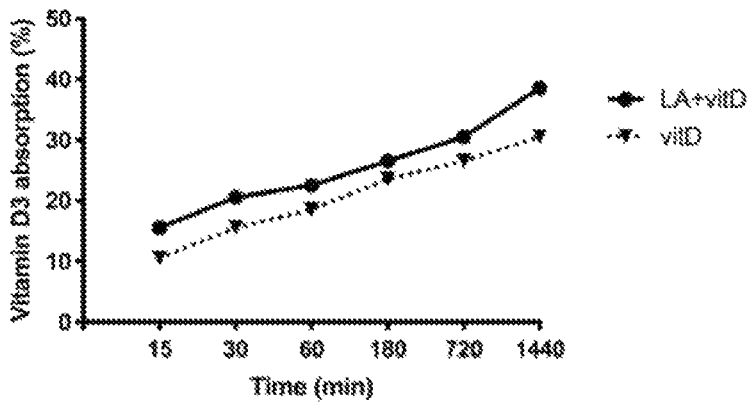
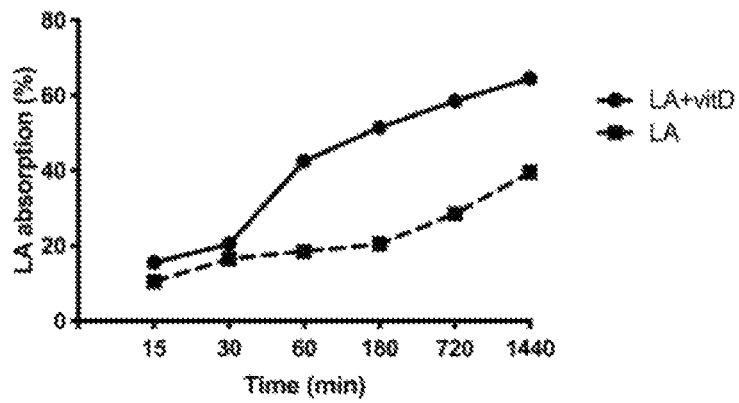
Figure 2(a), Figure 2(b) e Figure 2(c): quantifications of permeability of the blood–brain barrier of vitD and LA.

Figure 3(a), Figure 3(b) and Figure 3(c): cell viability analysis, production of ROS and mitochondrial activity in oxidative conditions; * $p < 0.05$ vs control; ** $p < 0.05$ vs LA; φ $p < 0.05$ vs vitD; φφ $p < 0.05$ vs $H_2O_2$; bars $<0.05$ between the treatments

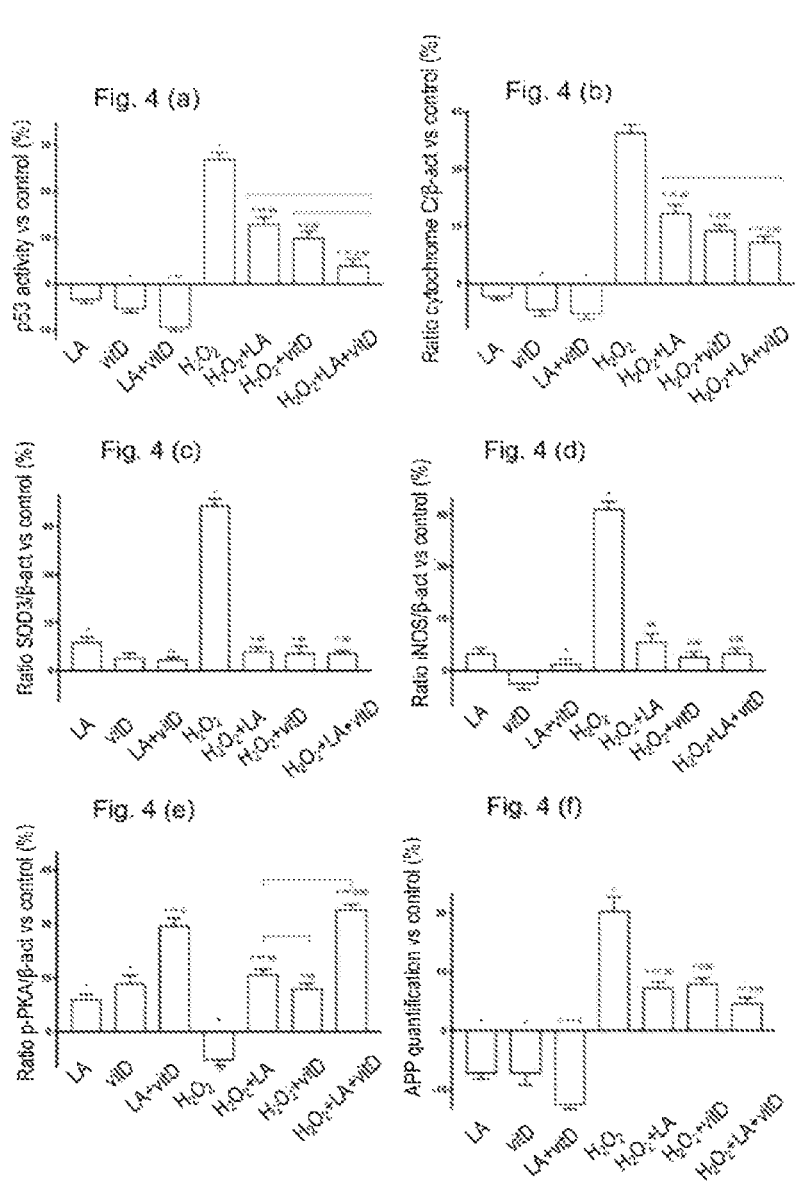
Figure 4(a), 4(b), 4(c), 4(d), 4(e) and 4(f): activity of the kinase and densitometric analysis of the intracellular pathways involved in oxidative stress; * $p < 0.05$ vs control; ** $p < 0.05$ vs LA; φ $p < 0.05$ vs vitD; φφ $p < 0.05$ vs $H_2O_2$; bars $p < 0.05$ between the treatments.

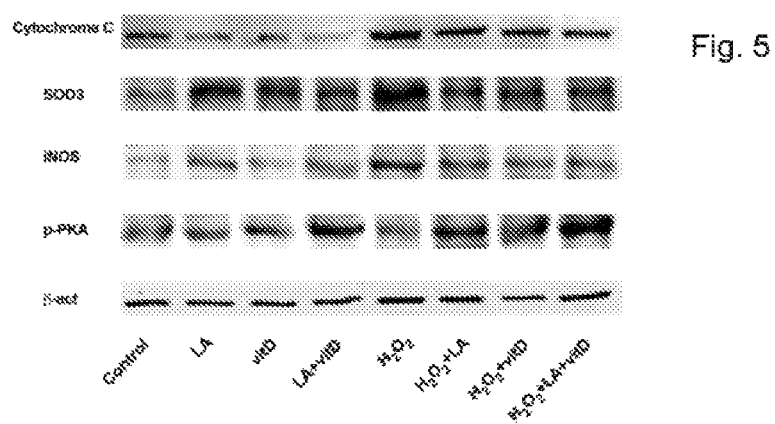
Figure 5: Western blot of SOD3, iNOS, p-PKA and β-act in astrocytes under oxidative stress.

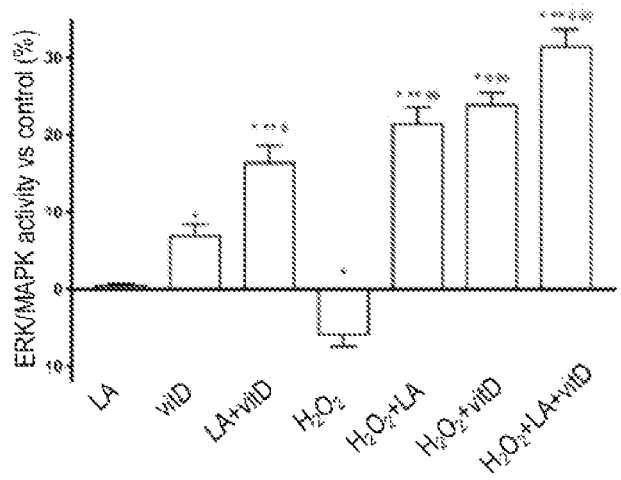
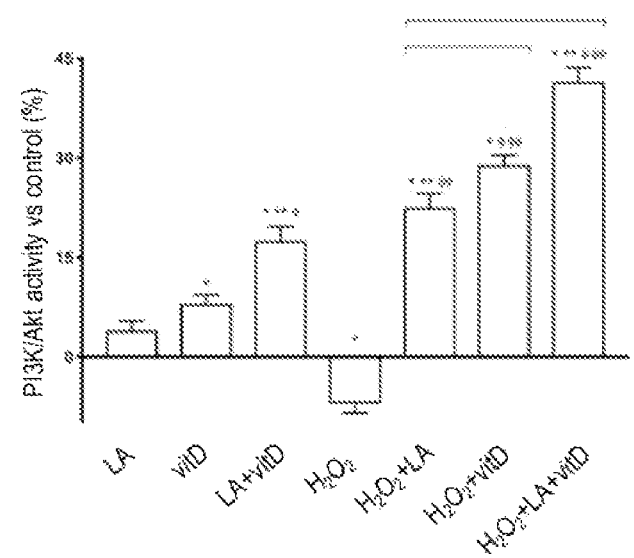
Figure 6(a), 6(b): activity of ERKs/MAPK and PI3K-Akt measured in astrocytes in oxidative conditions; * p <0.05 vs control; ** p <0.05 vs LA; φ p <0.05 vs vitD; φφ p <0.05 vs H2O2, bars p <0.05 between the treatments.

Figure 7(a), 7(b), 7(c): cell viability, production of ROS and quantification of intracellular iron measured in astrocytes pre-treated with $Fe^{3+}$; * $p < 0.05$ vs control; ** $p < 0.05$ vs LA; φ $p < 0.05$ vs vitD; φφ $p < 0.05$ vs $Fe^{3+}$, bars $p < 0.05$ between the treatments.

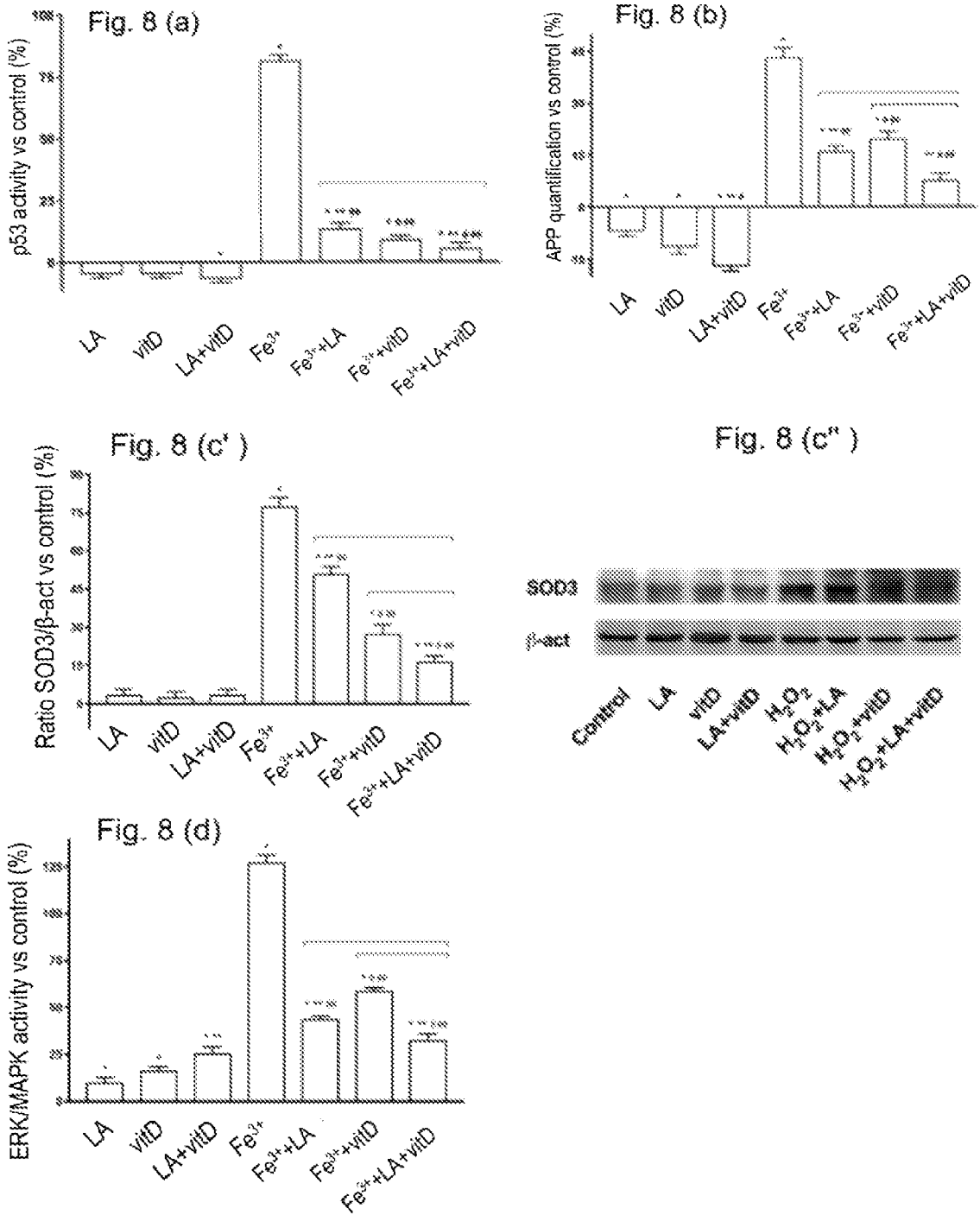
Figure 8(a), 8(b), 8(c'), 8(c'') and 8(d): activity p53, APP and ERK / MAPK, and densitometric analysis and Western blot of the SOD3 expression in the astrocytes pre-treated with $Fe^{3+}$; * $p < 0.05$ vs control; ** $p < 0.05$ vs LA; φ $p < 0.05$ vs vitD; φφ $p < 0.05$ vs $Fe^{3+}$, bars $p < 0,05$ between the treatments.

COMPOSITION COMPRISING LIPOIC ACID AND VITAMIN D FOR THE PREVENTION AND THE TREATMENT OF NEURODEGENERATIVE DISEASES AND PERIPHERAL NEUROPATHIES

CROSS-REFERENCE TO RELATED APPLICATIONS

This application is a § 371 national phase of International Application No. PCT/IB2019/057612, filed on Sep. 10, 2019, which claims the benefit of Italian Application No. 102018000008450, filed on Sep. 10, 2018, all of which applications are incorporated by reference herein.

The present invention regards a composition comprising lipoic acid, or an acceptable pharmaceutical or food grade salt thereof or a derivative thereof, and a vitamin D, preferably vitamin D3 and/or vitamin D2. Furthermore, the present invention regards said composition for use in a method for the therapeutic and/or non-therapeutic treatment of diseases, symptoms and/or disorders related with cerebral aging (biological), in particular for use in a method for the treatment of neurodegenerative diseases, and/or for use in the treatment of peripheral neuropathies.

Aging is an extremely complex multi-factorial process characterised by a gradual and continuous loss of physiological functions, particularly marked in the brain.

It is widely known that cerebral biological aging is not strictly related to chronological aging and the scientific community is trying to slow cerebral biological aging and reduce the possibility of suffering from diseases related to cerebral aging like the neurodegenerative diseases. The cognitive fragility is emerging as one of the greatest health menaces of the twenty-first century. Life expectancy continues to grow but the prevailing of cognitive decline is on the rise at the same time. This is turning into a serious social problem which is a source of distress and increase of costs for individuals, families and the national health systems.

A common distinctive sign of aging and diseases related with aging, in particular neurodegenerative diseases, is the increase of oxidative stress and simultaneous failure of antioxidant defence systems. Even though aging is an inevitable event, an increasing volume of data confirms that taking antioxidants combined with symptomatic drugs reduces oxidative stress and improves the cognitive functions in aging and the aging-related diseases. In particular, the brain is highly susceptible to the oxidative damage due to the high concentrations of polyunsaturated fatty acids and transition metals which are involved in the generation of the hydroxyl radical. In an adult brain, astrocytes are responsible for maintaining the neuronal and synaptic function. Oxidative stress plays a key role in the loss of astrocytes, mainly due to the highly active metabolism of mitochondria. According to the literature, the brain has poor catalyst activity and it has low levels of protective antioxidant enzymes.

Neurodegenerative diseases are a heterogeneous group of disorders characterised by progressive and selective neuronal death which leads to the degeneration of specific cerebral regions mainly caused by the natural aging process and by other factors not related with aging. The most common neurodegenerative diseases are the Alzheimer's disease (AD), characterised by a progressive loss of cognitive functions, and by the Parkinson's disease (PD), characterised by motor symptoms correlated with dopaminergic neuronal loss in the substantia nigra. In the developing and adult brain, non-neuronal glial cells, in particular astrocytes, perform important functions which regulate the number of synapses and synaptic communication and support the neuronal health and homoeostasis. However, the functions of the astrocytes are altered in an aging brain and this contributes towards reducing the neuronal and synaptic function. It is known that oxidative stress plays a key role in the loss of astrocytes. Furthermore, the mitochondrial "free radicals" theory is one of the most studied theories to explain the molecular mechanism of aging; it is based on the endogenous production of reactive oxygen species (ROS) and on their harmful effect on mitochondria. Furthermore, nitrogen oxide (NO), when produced in high concentrations, functions as a source of toxic oxidants, called reactive nitrogen species. ROS reacts with lipids, proteins and nucleic acids, causing an oxidative damage and leading to a progressive decline of the cell functions. In any case, the organism has defence mechanisms based on antioxidant actions; a group of enzymatic molecules (for example superoxide dismutase, catalase and glutathione reductase) or non-enzymatic molecules (for example glutathione, melatonin, vitamins A, C and E and flavonoids) which play a crucial role in the maintenance of homoeostasis and cell viability. In some cases, the endogenous antioxidant system is not strong enough to fight the oxidative damage caused by the ROS and NO. Numerous studies aimed at studying the effects of dietary antioxidant supplementation in aging or in neurodegenerative diseases were conducted to this end.

Furthermore, the increase of oxidative stress and the simultaneous failure of antioxidant defence systems can be the cause of peripheral neuropathies.

Lastly, a typical mechanism of aging in a healthy subject is the selective accumulation of iron, which occurs in various regions of the brain, and types of cells, and it could affect the development of peripheral neuropathies. However, the accumulation of iron in specific cerebral regions, greater than that observed in a healthy aging, occurs in many neurodegenerative diseases and it is often associated with oxidative stress and cell damage. It is known that lipoic acid is a strong chelator of divalent metal ions and that vitamin D, in particular vitamin D3 and/or vitamin D2, is capable of preventing the damage induced by accumulation of iron. However, the processes involved in the accumulation of iron correlated with aging and inflammation induced by iron in specific regions and cerebral cells and/or of the peripheral nerves are currently scarcely understood.

The diseases of the nervous system can be classified into diseases of the central nervous system and diseases of the peripheral nervous system.

The expression peripheral nervous system is used to indicate the parts of the nervous system located outside the encephalon and the spinal cord.

The peripheral nervous system is the connection pathway between peripheral receptor organs, skin, muscles or glands and the central nervous system.

Peripheral neuropathy is the name given to any disease that affects the peripheral nervous system.

Depending on the anatomical distribution of the damage, peripheral neuropathies can be classified into: mononeuropathy (damage to a single nerve), multiple mononeuropathy or multineuropathy (damage to more than one nervous trunk simultaneously or consecutively and in an asymmetric fashion), polyneuropathies (bilateral and symmetrical involvement of the peripheral nerves, mainly distal), polyneuritis (a term used for inflammatory, acute or subcutaneous forms, often with increasing development), radiculopathy (affecting the nerve root), plexopathy (affecting the nervous plexus).

The damage could be local (trauma or compression), or generalised, determining radiculopathies and mononeuropathies in the former case and multineuropathies or polyneuropathies in the other case. Plexopathies may recognise both types of mechanisms.

They are classified according to the type of fibres involved (sensory, motor, autonomic or mixed), topographical distribution (distal or proximal), primarily affected nervous component (demyelinating, axonal, mixed or undetermined). They can be hereditary, or more frequently, acquired and lead to many primary damage mechanisms: toxic, metabolic, endocrines, infectious, deficiency, inflammatory or paraneoplastic.

Peripheral neuropathies are characterised by various combinations of motor, sensory, autonomic and trophic signs and symptoms. Subjective disorders arise from a sensation of low sensitivity, paraesthesia, dysesthesia and paroxysmal or continuous pains. Subjective disorders of a low tactile or thermal-pain sensitivity could be reported. Furthermore, patients may complain of difficulty in the upright position and when moving due to low proprioceptive sensitivity. Vegetative disorders may regard vasomotion and sweating. In severe or chronic forms, there may be a muscle hypertrophy.

Peripheral neuropathy is diagnosed by means of a clinical test and electrophysiological findings, in particular electroneurography. This test allows to define the site of damage and the affected type of fibre, to distinguish axonal, demyelinating and mixed forms.

In the context of the present invention, the expressions "peripheral neuropathy diseases" and "peripheral neuropathies" are used as synonyms.

Thus, in the society there is a high demand for suitable treatments for conditions related with cerebral aging (cerebral biological aging), in particular for the treatments of neurodegenerative diseases, and/or for the treatments of peripheral neuropathies.

The pharmaceutical compositions (drugs) or dietary supplements or nutraceutical products currently available on the market for the therapeutic and non-therapeutic treatment of diseases, symptoms and/or disorders related with cerebral aging, in particular for the treatment of neurodegenerative diseases, such as for example Alzheimer's disease (AD) and/or Parkinson's disease (PD), and/or for the treatment of peripheral neuropathies, are often ineffective or just partially effective. Furthermore, said drugs or dietary supplements or nutraceutical products can cause adverse effects even very severe ones.

The technical problem addressed and solved by the present invention lies in providing a valid solution for the effective therapeutic and non-therapeutic treatment of diseases, symptoms and/or disorders related with cerebral aging, in particular for the treatment of neurodegenerative diseases, such as for example Alzheimer's disease (AD) and/or Parkinson's disease (PD), and/or for the treatment of peripheral neuropathies, capable of overcoming the currently unresolved drawbacks of the prior art, in particular as concerns lack of effectiveness and/or presence of adverse effects. Furthermore, the technical problem addressed and solved by the present invention lies in providing a valid solution for the non-therapeutic treatment of subjects in cerebral aging stage (cerebral biological aging) capable of slowing such process in an effective manner and without adverse effects.

In order to overcome these technical problems, the present invention provides a composition (pharmaceutical composition, nutraceutical composition, dietary supplement or medical device composition) comprising, as active ingredients, lipoic acid or an acceptable pharmaceutical or food grade salt thereof or a derivative thereof, and a vitamin of group D, preferably vitamin D3 (cholecalciferol) and/or vitamin D2 (ergocalciferol). Said composition is capable of effectively and rapidly treating diseases, symptoms or disorders caused by or related with cerebral aging (cerebral biological aging), in particular for the treatment of neurodegenerative diseases, and/or for the treatment of peripheral neuropathies, both in diseased subjects and in healthy subjects (not yet defined diseased).

Furthermore, the present invention provides a composition without the adverse effects present in the treatments of the prior art, easy to prepare and economically advantageous.

These and other objects, which will be clear from the detailed description that follows, are attained by the compositions and the mixtures of the present invention due to the technical characteristics claimed in the attached claims.

Following an intense research and development step, the Applicant found that the administration of the composition according to the present invention is capable of effectively and rapidly treating the diseases, symptoms and/or disorders caused by or related with cerebral (biological) aging, in particular, neurodegenerative diseases, and generally slowing cerebral aging, and/or for the treatment of peripheral neuropathies. Said pharmacological activity for the therapeutic or non-therapeutic treatment is due to the particular combination of the two active ingredients present in the composition, such as lipoic acid and vitamin of group D, preferably vitamin D3 and/or vitamin D2, and the synergic effect thereof. As a matter of fact, the two active ingredients act in a synergic fashion in the treatment of the astrocytes under oxidative stress conditions and it allows to prevent the oxidative damage in the astrocytes depending on accumulation of $Fe^{3+}$ as illustrated in detail in the experimental part.

DESCRIPTION OF THE FIGURES

FIG. 1(a): time-dependent and dose-response studies of lipoic acid (LA) measured in astrocytes FIG. 1(b): time-dependent and dose-response studies of 50 μM LA combined with 100 nM vitamin D3 (vitD) measured in astrocytes.

FIG. 2 (a), (b), (c): quantifications of permeability to the blood-brain barrier of vitD and LA.

FIG. 4 (a), (b), (c), (d), (e) and (f): kinase activities and densitometric analysis of the intracellular pathways involved in oxidative stress; (a) and (f) measurements of activities p53 and APP respectively; (b), (c), (d) and (e) densitometric analysis of the expressions of cytochrome C, SOD3, iNOS and p-PKA obtained by analysing the Western blot on astrocyte lysates under oxidative conditions.

FIG. 5: Western blot of SOD3, iNOS, p-PKA and β-actin in astrocytes under oxidative conditions.

FIGS. 6(a) and (b): activities of ERKs/MAPK and PI3K-Akt measured in astrocytes under oxidative conditions.

FIG. 8(a), (b), (c'), (c") and (d): measurements of the p53, APP and ERK/MAPK activities, and densitometric analysis and Western blot of the expression of SOD3 in astrocytes pre-treated with $Fe^{3+}$.

Figure 3:
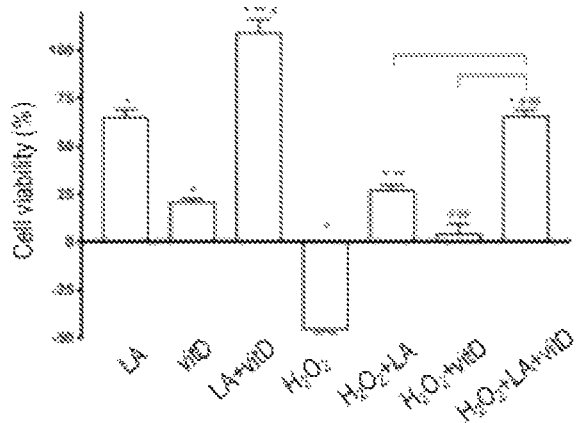
FIG. 3 (a), (b), (c): cell viability analysis, production of ROS and mitochondrial activity under oxidative conditions.
Figure 3:
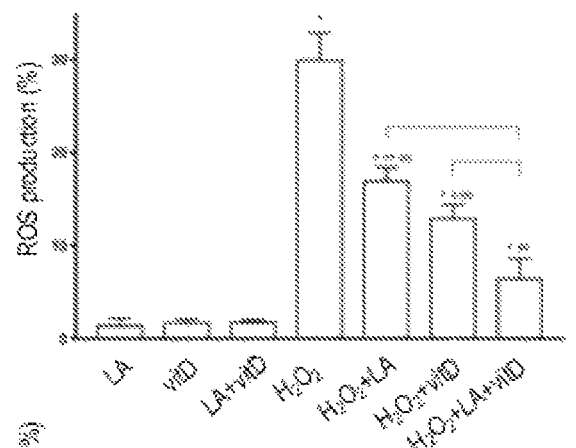
Figure 3:
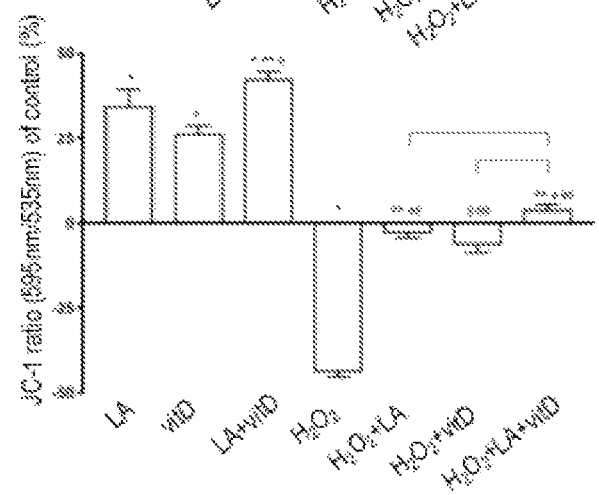

Forming an object of the present invention is a composition (in short composition of the invention) comprising
(i) a mixture (in short mixture of the invention) comprising, or alternatively, consisting of:
(I) lipoic acid or an acceptable pharmaceutical or food grade salt thereof or a derivative thereof;
(II) a vitamin of group D;
and, optionally, said composition further comprises,
(ii) at least one food grade or pharmaceutical additive and/or excipient.

Lipoic acid (abbreviated as LA) was isolated for the first time in 1951 from liver extracts, by the American biochemists L. J. Reed and I. C. Gunsalus. Lipoic acid is produced by our organism at small amounts, but it can be taken, though at small amounts, through the diet (broccoli, brewer's yeast and offals are the main sources thereof).

Lipoic acid is a molecule having a chiral centre and it is produced by the human organism in the chiral R form (R-lipoic acid, IUPAC name (R)-5-(1,2-dithiolan-3-yl)pentanoic acid). Synthetic lipoic acid (also referred to as alpha-lipoic acid, in the context of the present invention) is instead a mixture of the chiral R and S forms (racemic form).

In the context of the present invention, in the composition according to the invention comprising (I) and (II), the expression "lipoic acid" interchangeably refers both to the racemic form (alpha-lipoic acid) and the chiral R form.

The composition of the present invention may comprise lipoic acid in its racemic form (alpha-lipoic acid or (RS)-lipoic acid) or, alternatively, in its chiral R form (R-lipoic acid). Preferably, the composition of the present invention comprises lipoic acid in the racemic form (alpha-lipoic acid) or an acceptable pharmaceutical or food grade salt thereof or a derivative thereof.

Lipoic acid is a low molecular weight molecule, characterised by a good solubility both in hydrophilic environment and in lipophilic environment. In nature it exists in two forms: as a cyclic disulfide (oxidised form) or as an open chain, called dihydrolipoic acid, which has two sulfhydryl groups; the two forms are easily interconvertible by redox reactions. Lipoic acid is characterised by a high antioxidant capacity, due to its particular chemical structure and, mainly, due to the presence of the disulfide bridge which acts as an electron acceptor. As an antioxidant, lipoic acid not only serves as a scavenger of the reactive oxygen species (ROS), but it also has transition metal chelating properties.

The expression "derivative" of lipoic acid, is used in the context of the present invention, in the composition according to the invention comprising (I) and (II), to indicate a derivative of lipoic acid, preferably alpha-lipoic acid, known to the man skilled in the art, having antioxidant properties similar to lipoic acid, such as for example, the reduced form of lipoic acid such as dihydrolipoic acid (DHLA).

In the composition according to the invention, in the composition according to the invention comprising (I) and (II), the expression "vitamin of group D" is used to indicate a compound belonging to a group of liposoluble pro-hormones of natural origin comprising vitamin D1 (ergocalciferol and lumisterol 1:1), vitamin D2 (ergocalciferol), vitamin D3 (cholecalciferol); vitamin D4 (dihidroergocalciferol), vitamin D5 (sitocalciferol), and the mixtures thereof. Preferably, the expression (II) "vitamin of group D" is used to indicate vitamin D3 or vitamin D2 of a mixture of vitamin D3 and vitamin D2.

In the context of the present invention, in the composition according to the invention comprising (I) and (II), the expression "a vitamin of group D, or the derivatives thereof" is used to indicate complexes of compounds part of the group of vitamins of group D, preferably vitamin D3 and/or vitamin D2, protection derivatives, such as compounds part of the vitamins of group D whose functional groups are protected with suitable protector groups, or metabolic precursors, known to the man skilled in the art.

In a preferred embodiment, in the composition according to the invention comprising (I) and (II), said (II) vitamin of group D is vitamin D3 or cholecalciferol (CAS N. 67-97-0) or a derivative thereof as defined above.

In an alternative preferred embodiment, in the composition according to the invention comprising (I) and (II), said (II) vitamin of group D is vitamin D2 or ergocalciferol (CAS N. 50-14-6) or a derivative thereof as defined above.

In a further preferred embodiment, in the composition according to the invention comprising (I) and (II), said (II) vitamin of group D is a mixture of vitamin D3 or a derivative thereof and vitamin D2 or a derivative thereof. In said embodiment said vitamins can be at a by weight ratio (vitamin D3:vitamin D2) comprised in the range from 10:1 to 1:10, preferably from 5:1 to 1:5, more preferably about 1:1.

In a preferred embodiment, the (i) mixture of the present invention comprises (I) lipoic acid in the racemic form (alpha-lipoic acid) or an acceptable pharmaceutical or food grade salt thereof or a derivative thereof and (II) vitamin D3 or a derivative thereof.

In a preferred embodiment, the (i) mixture of the present invention comprises (I) lipoic acid in the racemic form (alpha-lipoic acid) or an acceptable pharmaceutical or food grade salt thereof or a derivative thereof and (II) vitamin D2 or a derivative thereof.

In a preferred embodiment, the (i) mixture of the present invention comprises (I) lipoic acid in the racemic form (alpha-lipoic acid) or an acceptable pharmaceutical or food grade salt thereof or a derivative thereof and (II) a mixture of vitamin D3 or a derivative thereof and of vitamin D2 or a derivative thereof, preferably at a by weight ratio (vitamin D3:vitamin D2) comprised in the range from 10:1 to 1:10, preferably from 5:1 to 1:5, more preferably about 1:1.

In the composition of the invention, according to the aforementioned embodiments (lipoic acid and vitamin D3 and/or vitamin D2), each component (I) and (II) can be present at the amounts defined below. Preferably, said (I) lipoic acid is present in said (i) mixture of the invention at an amount by weight comprised from 90% to 99.9%, with respect to the total weight of the mixture, preferably from 98% to 99.9%, more preferably from 99% to 99.9%, and it is present in the composition of the invention at an amount by weight from 100 mg to 1000 mg, with respect to the total weight of the composition, preferably from 200% to 800%, more preferably from 400% to 800%.

Preferably, said (II) vitamin of group D, preferably vitamin D3 (or cholecalciferol) and/or vitamin D2 (or ergocalciferol), is present in said (i) mixture of the invention at an amount by weight comprised from 0.001% to 10%, with respect to the total weight of the mixture, preferably from 0.001% to 1%, more preferably from 0.001% to 0.01%, and it is present in the composition of the invention at an amount by weight from 2 µg to 1000 µg, with respect to the total weight of the composition, preferably from 5 µg to 100 µg, more preferably from 5 µg to 50 µg.

Besides the (i) mixture of the invention comprising (I) and (II) and, optionally, besides the (ii) additives and/or excipients, the composition according to the present invention may further comprise other active ingredients such as, by way of non-limiting example, anti-inflammatories, antioxidants, probiotics, antacids, vitamins of a group different from group D (for example vitamins of group A, B, C, E and K) and mineral salts, N-acetyl cysteine, homotaurine and L-acetyl carnitine, phosphatidylserine and plant extracts e.g. withania somnifera and bacopa, nervonic acid and minerals, such as Zn, Mg, etc.

Forming an object of the present invention is the composition of the invention comprising (I) and (II) in light of the description above, preferably comprising (I) lipoic acid and (II) vitamin of group D3 and/or vitamin of group D2, wherein said composition is for use in a preventive and/or curative treatment of diseases, symptoms and/or disorders related with cerebral (biological) aging in a needy subject; in particular, a method for the preventive and/or curative treatment of neurodegenerative diseases, symptoms and/or disorders related with said neurodegenerative diseases.

Neurodegenerative diseases are a varied set of diseases of the central nervous system, sharing a chronic and selective neuronal cell death process. Depending on the type of disease, neuronal deterioration may entail cognitive deficit, dementia, motor alteration, behavioural and psychological disorders.

The most common neurodegenerative diseases include:
Alzheimer's disease (AD); Parkinson's disease (PD); Huntington's disease; amyotrophic lateral sclerosis (ALS); frontotemporal dementia (FTD or EOD or early-onset dementia); progressive supranuclear palsy (PSP or Steele-Richardson-Olszewski syndrome); Lewy body dementia (LBD); Creutzfeldt-Jakob disease (CJD) and Gerstmann-Sträussler-Scheinker syndrome (GSS); neurodegenerative diseases; age-related cognitive decline, attention and mnemonic cognitive abilities deficit.

In the context of the present invention, the expression "neurological diseases" or the expression "diseases, symptoms and/or disorders related with cerebral (biological) aging" does not include hearing loss diseases, in particular it does not include hearing loss due to aging.

The Alzheimer-Perusini disease, also referred to as Alzheimer's disease, early-onset dementia of the Alzheimer's type, primary degenerative dementia of the Alzheimer's type or simply Alzheimer, is the most common form of progressively disabling degenerative dementia with on-set mainly at pre-senile age (beyond 65 years of age, but it could also occur at a prior stage). In DSM-5 it is cited as a more severe or milder neurocognitive disorder related with Alzheimer's disease.

Parkinson's disease, often referred to as Parkinson's syndrome, Parkinson, idiopathic Parkinson's disease, Primary Parkison's disease, hypokinetic rigid syndrome or paralysis agitans, is a neurodegenerative disease. The motor symptoms typical of the condition result from the death of the cells that synthesise and release dopamine. Such cells are found in the substantia nigra, a mesencephalic region.

Huntington's disease is a neurodegenerative genetic disease that affects muscle coordination and leads to a cognitive decline and psychiatric problems. Its onset is typically at the middle age; it is the most frequent genetic-related disease in neurological clinical pictures with abnormal involuntary movements.

Amyotrophic lateral sclerosis, or ALS, also referred to as Lou Gehrig's disease or Charcot's disease or motor neuron disease, is a progressive neurodegenerative disease of the motor neuron, which selectively affects the motor neurons. ALS is characterised by muscle rigidity, muscle contraction and gradual weakness due to loss of muscle strength. This leads to difficulty of speech, of swallowing and, lastly, of breathing.

The expression frontotemporal dementia (abbreviated as FTD) identifies a heterogeneous group of non-Alzheimer's neurodegenerative dementia characterised by the presence of degenerative-atrophy alteration of the frontal and temporal cerebral lobes. This is a general expression covering various diseases or alternatively a disease with several variants; it is also referred to as early-onset dementia (as opposed to the more commonly senile dementia like vascular dementia) due to the onset usually at around 50-60 years of age, and it can often be confused with the early form of Alzheimer's disease; however, whereas in the latter memory is the mainly damaged function, at the onset signs of FTD are manifested by sudden change of personality and strange behavioural-motor conduct in absence of pre-existing psychiatric or neurological diseases, and—only subsequently—by a partial loss of memory as well as progressive cognitive and motor deficit. The average survival rate is of about 7-8 years. In DSM-5 it is cited as a more severe or milder frontotemporal neurocognitive disorder.

Progressive supranuclear palsy (PSP) or the Steele-Richardson-Olszewski syndrome is a neurodegenerative disease described for the first time in 1964. Neurodegeneration entails atrophy at mesencephalic level and at the level of other cerebral structures including the subthalamic nucleus, globus pallidus, the nuclei of the pons and substantia nigra. PSP falls within a group of neurological disorders classified as "Parkinson-Plus" or "Atypical parkinsonism" with symptoms that remind of the Parkinson's disease, while other characteristics are clearly different.

Dementia with Lewy bodies (or DLB) is a neurodegenerative disease, a form of dementia similar to Alzheimer's disease but with an earlier onset and often correlated with the Parkinson's disease and Parkinson's syndromes.

Creutzfeldt-Jakob disease (CJD), originally described in the twenties of the twentieth century by Hans Gerhard Creutzfeldt and Alfons Maria Jakob, is a rare neurodegenerative disease which leads to a form of fatal progressive dementia. The clinical syndrome is characterised by mainly cortical multi-sector deficit with loss of memory, change of character, hallucinations, dysarthria, myoclonus, postural rigidity and convulsions.

Gerstmann-Sträussler-Scheinker syndrome (GSS) is a very rare and strictly familial neurodegenerative disease with autosomal dominant inheritance, classifiable as transmissible spongiform encephalopathy (TSE).

Forming an object of the present invention is the composition of the invention comprising (I) and (II) in light of the description above, preferably comprising (I) lipoic acid and (II) vitamin of group D3 and/or vitamin of group D2, wherein said composition is for use in a preventive and/or curative treatment of peripheral neuropathies, and symptoms and/or disorders related with said peripheral neuropathies, in a needy subject.

Preferably, the composition of the invention comprising (I) and (II) in light of the description above, preferably comprising (I) lipoic acid and (II) vitamin of group D3 and/or vitamin of group D2, is for use in a method for the treatment of the following peripheral neuropathies: diabetic neuropathy, carpal-tarsal-ulnar tunnel syndrome, cervicobrachialgia, herpes zoster, intervertebral disc herniation, sciatic neuralgia-lower back pain, Guillain-Barre syndrome, toxic and deficiency neuropathies (such as, drug-related neuropathy, alcoholic neuropathy), infectious neuropathies (such as, HIV infection-related neuropathies, cytomegalovirus-related neuropathies).

Diabetes is the most frequent cause of diabetic neuropathy, peripheral neuropathy which is expressed with various clinical variants: symmetrical polyneuropathies, focal neuropathy and mixed forms. The incidence of diabetes mellitus (DM) is calculated to affect about 6% of the general population; the prevalence of the neuropathy is about 7% upon the occurrence of DM rising up to 25-30% after 20 years in patients suffering from diabetes II.

Carpal tunnel syndrome is the most common entrapment peripheral neuropathy. It is idiopathic in most cases. Carpal tunnel syndrome is manifested by the occurrence of pains and paraesthesia, especially nocturnal, on the first three fingers and the lateral half of the fourth finger, as well as the lateral half of the palm. Over time, the pains and paraesthesia are also irradiated to the forearm and even the arm at times.

Radial tunnel syndrome is the compression of the radial nerve in the proximal portion of the forearm. The symptoms comprise forearm and elbow pain.

Tarsal tunnel syndrome entails ankle, foot and at times finger pain, caused by the compression or lesion of the posterior tibial nerve.

Cervicobrachialgia is caused by the compression of a cervical nerve; it is characterised by pain originating from the posterior cervical region leading to a functional limitation of the flexion/extension and rotational movements of the neck, irradiated to one or both upper limbs.

Herpes zoster, commonly referred to as shingles, is a viral disease of the skin and of the nerve endings, caused by the varicella zoster virus. This is a ganglion-radicular syndrome. The clinical picture of herpes zoster is characterised by pain, skin, neurological and infectious manifestations in the broad sense.

Intervertebral disc herniation is manifested in the cervical and lumbar regions: due to the stresses that these parts of the spinal cord are subjected to, intervertebral discs are more likely to suffer from degenerative processes. Hence, there could be fractures regarding the outer fibrous ring and subsequent herniations of the disc which projects from the intervertebral space, compressing the nervous structures.

Sciatic neuralgia, or sciatica, is characterised by the lesion of the sciatic nerve at radicular or torcular level mainly in sensitive fibres. Symptoms essentially consist of intense pain, excruciating at times, in the area of distribution of L5-S1 i.e., in the inferior gluteal region, in the posterior face of the thigh and of the leg.

Guillain-Barre syndrome is an acute polyradiculoneuritis. This is the most frequent and known cause of ascending paralysis: its clinical presentation shows acute or subacute onset of muscle weakness on the lower limbs and ascending evolution reaching its lowest point within four weeks.

The most frequently observed toxic neuropathies are those caused by:
  intoxication by metals, such as lead, mercury, thallium and arsenic
  drugs, such as antiblastics, chemotherapics, antiarrhythmics, antirheumatics Infectious neuropathies comprise numerous clinical-pathological entities, including neuropathies related with human immunodeficiency virus infections and cytomegalovirus-related neuropathies.

In the context of the present invention, the expression composition for use in a method for the treatment of peripheral neuropathies related with renal diseases does not include the treatment of inflammations in a population with chronic renal disorders (chronic kidney disease, abbreviated as CKD) at the end stage (end-stage renal disease or stage-5, abbreviated as ESRD) in haemodialysis (abbreviated as HD).

According to an embodiment of the invention, the composition of the present invention comprises amounts of (I) and (II) such to guarantee the administration, to needy subjects, of daily doses comprised between:
  300 and 800 mg of (I) lipoic acid;
  5 and 50 micrograms of (II) vitamin D, preferably vitamin D3 and/or vitamin D2.

The composition of the invention can be administered to the needy subjects once or several times a day depending on the condition of the patient and on the amounts of (I) and (II) comprised in the composition.

Furthermore, the present invention describes a method for the preventive and/or curative treatment of diseases, symptoms and/or disorders related with cerebral (biological) aging, wherein said treatment comprises the administration of the composition of the invention as defined above to a needy subject; in particular, a method for the preventive and/or curative treatment of neurodegenerative diseases as defined above and/or symptoms or disorders related with said neurodegenerative diseases; and/or a method for the preventive and/or curative treatment of peripheral neuropathies, and of symptoms and/or disorders associated with said peripheral neuropathies.

Forming an object of the present invention is the non-therapeutic use of the composition of the invention as defined above for the non-therapeutic treatment of symptoms or disorders associated with cerebral (biological) aging in a needy subject.

Forming an object of the present invention is the non-therapeutic use of the composition of the invention as defined above for the non-therapeutic treatment of slowing cerebral (biological aging) in a needy subject.

Lastly, forming an object of the present invention is a pharmaceutical composition, nutraceutical composition, dietary supplement product or a food product or a food for special medical purpose or a medical device composition comprising or, alternatively, consisting of the composition of the present invention comprising (I) and (II) in light of the description above, preferably comprising (I) lipoic acid and (II) vitamin of group D3 and/or vitamin of group D2.

The expression "medical device" in the context of the present invention is used according to the meaning laid down by the Italian Legislative Decree n° 46, dated 24 Feb. 1997 and according to the new Medical Devices Regulation (UE) 2017/745 (MDR), i.e. it indicates a substance or another product, used alone or in combination, designated by the manufacturer to be used in humans for the diagnosis, prevention, control, therapy or attenuation of a disease, the product not exercising the main action, in or on the human body, for which it is designated, neither using pharmacological or immunology means nor by means of a metabolic process but the function thereof can be coadjuvated by such means.

The composition of the present invention, comprising (I) and (II) in light of the description above, preferably comprising (I) lipoic acid and (II) vitamin of group D3 and/or vitamin of group D2, can be, by way of non-limiting example, in a liquid form, such as a solution, two-phase liquid system, suspension or syrup, in a semi-solid form, such as gel, cream or foam, or solid form, such as powder, granules, chips, aggregates, capsules, tablets, bars and equivalent forms.

Preferably, the composition of the invention is for oral use, preferably in solid or liquid form.

For the sake of clarity, with the aim of achieving the object of the present invention, the active ingredients of the mixture of the present invention (I) and (II) may also be administered separately (preferably at a time interval ranging from 30 minutes to 60 minutes) and in any order but, preferably, (I) and (II) are administered to a subject simultaneously, even more preferably in a single composition so as to obtain a more rapid effect and for ease of administration.

When the active ingredients (I) and (II) are administered in a single composition, said single composition corresponds to the composition of the present invention.

The expression "treatment method" in the context of the present invention is used to indicate an action, comprising the administration of a substance, or mixture of substances or combination thereof, with the aim of eliminating, reducing/decreasing or preventing a pathology or disease and its symptoms or disorders.

Unless specified otherwise, the indication that a composition "comprises" one or more components or substances means that other components or substances can be present besides the one, or the ones, indicated specifically.

The composition of the present invention shall be deemed indistinctly for human or veterinarian use, i.e. as a preparation to be applied to animals by means of the uses and methods known to the man skilled in the art.

As illustrated in the experimental part indicated below, the compositions of the present invention are suitable for the effective treatment, both therapeutic and non-therapeutic, of diseases, symptoms and/or disorders related with cerebral (biological) aging, specifically for the treatment of neurodegenerative diseases as defined above and/or symptoms or disorders associated with said neurodegenerative diseases, in particular, in absence of significant adverse effects. These results support the concept of synergic effect of the single components of the composition of the invention and which act in a synergic fashion in the treatment of astrocytes in oxidative stress conditions and allows to prevent the oxidative damage in astrocytes depending on accumulation of $Fe^{3+}$, as illustrated in detail in the experimental part.

Embodiments of the present invention are indicated below:

FR1. A composition comprising
(i) a mixture comprising, or alternatively, consisting of:
(I) lipoic acid or an acceptable pharmaceutical or food grade salt thereof or a derivative thereof;
(II) a vitamin of group D or a derivative thereof; and, optionally,
(ii) at least one food grade or pharmaceutical additive and/or excipient.

FR2. The composition according to FR1, wherein said (II) vitamin of group D is a vitamin D3 or cholecalciferol or a derivative thereof.

FR3. The composition according to FR1 or FR2, wherein said (I) lipoic acid is the racemic form of lipoic acid or acceptable pharmaceutical or food grade salt thereof or a derivative thereof.

FR4. The composition according to any one of the preceding FRs, wherein said composition is for use in a method for the preventive and/or curative treatment of a disease, symptom and/or disorder associated with the cerebral aging in a needy subject.

FR5. The composition for use according to FR4, wherein said composition is for use in a preventive and/or curative treatment of a neurodegenerative disease and/or of symptoms or disorders associated with said neurodegenerative disease.

FR6. The composition for use according to FR5, wherein said neurodegenerative disease is selected from among Alzheimer's disease (AD), Parkinson's disease (PD), Huntington's disease, amyotrophic lateral sclerosis (ALS), frontotemporal dementia (FTD or early-onset dementia), progressive supranuclear palsy (PSP or Steele-Richardson-Olszewski syndrome), Lewy body dementia (LBD), Creutzfeldt-Jakob disease (CJD) and Gerstmann-Sträussler-Scheinker disease (GSS).

FR7. The composition for use according to any one of FR4-FR6, wherein said composition is for oral use in said needy subject.

FR8. Non-therapeutic use of the composition according to any one of FR1-FR3, wherein said composition is for use in a method for the non-therapeutic treatment of a symptom or disorder associated with the cerebral aging in a needy subject.

FR9. Non-therapeutic use of the composition according to any one of FR1-FR3, wherein said composition is for use in a method for the non-therapeutic treatment of slowing the cerebral aging in a needy subject.

Experimental Tests

Materials and Methods

Isolation and Culture of Astrocytes.

The cultures of mouse astrocytes were prepared from male and female C57BL/6 baby mice, following a known conventional technique according to the national guidelines for the use and care of laboratory animals. Basically, within 24 hours from birth, the baby mice were euthanized and the corticals were cut, 25 minced, mechanically digested and left to rest for 30 minutes at ambient temperature. The cell suspension was then centrifuged at 800 rpm (revolutions per minute) for 5 minutes. The pelleted cells were resuspended in neuronal basal medium (Sigma-Aldrich), supplemented with fetal bovine serum at 5% (FBS, Gibco), penicillin/streptomycin 1% (Sigma-Aldrich) and L-glutamine 2 mM (Sigma-Aldrich), placed in multiple wells and kept in culture for 6 days prior to the treatment.

For the experiments: $1\times10^4$ cells on 96 wells were plated to study the cell viability through the MTT test, the amyloid precursor protein (APP) through the ELISA test, production of ROS through the colorimetric test, as described hereinafter: $1\times10^4$ cells on 96 black wells for analysing energy consumption through the fluorescence kit; $1\times10^6$ on 6 wells to determine the concentration of iron for colorimetric dosage; $1\times10^6$ on 6 wells for analysing the intracellular pathways activated by the Western blot analysis; $1\times10^6$ on 6 wells for analysing the activity of p53 and the activation of ERK/Akt; $4\times10^4$ on transwell support to study permeability, to quantify vitamin D3 (abbreviated as vitD) and alpha-lipoic acid (abbreviated as LA).

Before stimulations, the cells were kept in the modified Dulbecco's medium (DMEM, Sigma-Aldrich) without phenol red and fetal bovine serum (FBS, Sigma-Aldrich) and supplemented with 1% penicillin/streptomycin (Sigma-Aldrich) and 2 mM L-glutamine (Sigma-Aldrich) in an incubator at 37° C., 5% of CO 2 and 95% of humidity for 3 hours.

HUVEC culture.

Human umbilical endothelial cells (HUVECs) were used in this study with the aim of obtaining a co-culture along with the astrocytes as an in vitro BBB (blood brain barrier) experimental model. HUVECs were purchased from ATCC®. The cells were grown in EGM Media (Lonza) supplemented with 10% of FBS (Gibco) 1% of penicillin/streptomycin (Sigma-Aldrich) and 2 mM of glutamine (Sigma-Aldrich) at 37° C. in a humid atmosphere of 95% of air, 5% of $CO_2$. For the experiments, $1\times10^5$ HUVEC cells/ cm² were plated in the 6.5 mm apical compartment of Transwell with polyester membrane with 0.4 μm holes (Corning Costar, Sigma).

Experimental Protocol

The cells were used to study two different biological aspects involved in cerebral aging and in neurodegeneration: oxidative stress and iron-dependent damage.

The role played by vitamin D3 (vitD) and alpha-lipoic acid (LA) in physiological conditions were analysed in a first series of experiments. In this phase, dose-dependent and time-dependent (from 15 min to 1440 min) cell viability studies were conducted with LA (from 10 μM to 100 μM) to determine the optimal concentration thereof and then this concentration (50 μM) was maintained in all subsequent experiments. Thus, the combination with 50 μM LA and 100 nM vitD was studied in a time study (from 15 min to 1440 min) and then with a permeability test to determine each specific concentration through a BBB (blood brain barrier) experimental model.

In a second series of experiments, the role played by oxidative stress was studied through pre-treatment for 30 minutes with 200 μM of $H_2O_2$ on astrocytes. In particular, the capacity of vitD and LA—alone or combined—to prevent or restore the damage caused by oxidative stress was studied in the MTT test (standard colorimetric assay for measuring the activities of the enzymes that reduce the MTT to formazan, where the abbreviation MTT indicates the 3-(4,5-dimethylthiazol-2-yl)-2,5-diphenyltetrazolium) bromide compound). Furthermore, the measurement of the mitochondrial membrane potential (MMP), the quantification of the amyloid precursor protein (APP) and the Western blot analysis were conducted at 24 hours.

In a third series of experiments, in order to induce neurodegeneration, the cells were pre-treated with catalytic iron ($Fe^{3+}$) 300 μM for 6 days, and then treated with vitD and LA—alone or combined—for another 6 days to verify the protection provided by the combination of vitD and LA by analysing the viability, the production of ROS, the concentration of iron, the quantification of APP and the activated intracellular pathways.

MTT tests.

MTT based in vitro toxicology assay kit (Sigma-Aldrich) was conducted on a 96-well plate to determine cell viability after each stimulation as described in literature. At the end of the stimulation, the cells were incubated with MTT dye at 1% for 2 hours at 37° C. in an incubator, 5% di CO 2 and 95% of humidity; the violet formazan crystals were then dissolved in an equal volume of MTT solubilisation solution. Cell viability was determined by measuring absorbance at 570 nm with correction at 690 nm, using a spectrometer (VICTOR X4, multi-label plate reader) and calculated by comparing the results with the control.

Blood-brain barrier (abbreviated as BBB) experimental model.

The astrocytes were co-cultured with HUVEC cells according to the methods provided for by literature. Basically, 4×10⁴ astrocytes/cm² were plated on the basolateral side of the 6.5 mm flipped Transwells with polyester membrane with 0.4 μm hole-size (Corning Costar, Sigma-Aldrich) and left to attach for 4 hours. The Transwells were then positioned in the normal direction and the cells were left to grow for 48 hours. After this period of time, 1×10⁵ HUVEC cells/cm² were plated in the apical compartment. The inserts were then positioned in a 24-well plate. After 7 days of culture, the Transwells were treated and permeability studies were conducted. In order to understand the capacity of the tested substances to cross the blood-brain barrier, the means on the lower side of the Transwell was quantified over time (from 15 min to 1440 min) by measuring the concentration volume of vitD and LA.

Determination of lipoic acid.

The concentration of LA that crossed the blood-brain barrier (BBB) was measured as described in literature. Basically, at the end of the stimulations, the basolateral volume was analysed using the spectrometer (VICTOR X4, multi-label plate reader) at 320 nm and the absorbance regarding the standard curve obtained from LA (200 ng/ml). The results were expressed as means±SD (SD, standard deviation) (%) of absorption, normalised for the control.

Quantification of vitamin D.

The competitive ELISA assay kit (Fine Test) was used for detecting the metabolically active form of vitamin D3 (vitD), such as 25(OH)D3. At the end of each stimulation, 50 μl of each sample were collected and used immediately, following the manufacturer's instructions. 50 μl of biotin detection and 100 μl of SABC working solution were added to each sample and incubated at 37° C. for 30 minutes. At the end, the supernatants were disposed and then 90 μl of TMB plus substrate and 50 μl of stop solution were added. Lastly, the 96 wells were analysed in a 450 nm spectrometer (VICTOR X4 multi-label plate reader). Furthermore, a standard curve had to be drawn including the background (zero wells) to conduct a quantification.

Production of ROS.

The superoxide anion (anion $O_2^-$) release rate was used to examine the ROSs produced by the astrocytes after stimulations. After the treatment, 100 μL of cytochrome C were added in all samples (treated or not), 100 μL of superoxide dismutase were added in another sample for 30 minutes in an incubator (all substances were manufactured by Sigma-Aldrich). Absorbance was measured using a spectrometer (VICTOR X4, multi-label plate reader), at 550 nm and 02 was expressed as the mean±SD (SD, standard deviation) of nanomoles for cytochrome C reduced per microgram of protein with respect to the control on the percentage (%).

Mitochondrial membrane potential.

Mitochondrial membrane potential was analysed using the Oxygen consumption/Mito membrane potential dual assay kit, Cayman Chemical Company) following the manufacturer's instructions. Mitochondrial membrane potential was measured using JC-1 aggregates at a 560/590 nm excitation/emission and monomers at a 485/535 nm excitation/emission in a fluorescence spectrometer (VICTOR X4 multi-label plate reader). The results were expressed as means±SD (SD, standard deviation) (%) with respect to the control cells.

Activity of p53.

The activity of p53 was measured using the specific ELISA kit (p53 transcription factor analysis kit, Cayman Chemical), by examining the extracts of the nuclei obtained at the end of each stimulation following the manufacturer's instructions. The extraction of the nuclei was obtained through the conventional method using a complete buffer present in the kit. Basically, the cells were lysed with the ice-cold 1× complete hypotonic buffer supplemented with NP-40 and then centrifuged at 12000 g at 4° C. for 10 minutes. The pellet was solubilised with the ice-cold 1× complete nuclear extraction buffer supplemented with protease and phosphatase inhibitors and then centrifuged at 12000 g for 15 minutes at 4° C.; the supernatant was examined to analyse the activity of p53 regarding the quantification of the protein through the BCA assay (Thermo Fisher).

Quantification of the amyloid precursor protein (APP).

The quantification of the amyloid precursor protein (APP) was measured using the Amyloid Beta A4 protein ELISA kit (Sigma-Aldrich) on cell supernatants following the manufacturer's instructions. Basically, cell supernatants were collected at the end of the treatments and each sample was tested using the ELISA kit. A biotinylated detection antibody specific for the target protein was added in each well and the plate was incubated for 1 hour at ambient temperature. Then, after 45 of incubation with streptavidin conjugated with HRP, the TMB substrate solution was added for 30 minutes and the reaction was subsequently interrupted by adding a stop solution. The concentration of APP was determined by measuring the absorbance using a spectrometer (VICTOR X4 multi-label plate reader) at 450 nm and calculated by comparing the results with the APP standard curve.

ERK and Akt activation analysis.

ERK/MAPK and PI3K/akt activities were measured using ELISA InstantOne™ (Thermo Fisher) on cell lysates following the manufacturer's instructions. Basically, at the end of the treatments the cells were lysed with 100 µL of cell lysis buffer and 50 µL/well of each sample were tested in ELISA InstantOne microplate strips and the cocktail of antibodies was added in each well and incubated for 1 hour at ambient temperature on a microplate stirrer. At the end, the detection reagent was added to each well and after 20 minutes the reaction was interrupted by adding the stop solution to each well. The strips were measured by a spectrometer (VICTOR X4 multi-label plate reader) at 450 nm. The results were expressed in terms of absorbance (%) with respect to the control.

Iron quantification assay.

The iron analysis kit (Sigma-Aldrich) which measures ferrous iron (Fe 2-1, ferric iron ($Fe^{3+}$) and total iron (total iron–ferrous iron) in samples was used on astrocytes following the manufacturer's instructions. Absorbance at 593 nm was measured using the spectrometer (VICTOR X4, multi-label plate reader). The concentrations of ferric iron are equal to the total iron (sample plus iron reducer)—$Fe^{2+}$ (sample plus assay buffer). The concentration of iron was expressed in ng/ml.

Western Blot.

The cells were washed and then lysed in ice-cold Complete Tablet buffer (Roche) supplemented with 2 mM of sodium orthovanadate, 1 mM phenylmethylsulfonyl fluoride (PMSF; Sigma-Aldrich) and 1:100 Protease Inhibitor Cocktail mixture (Sigma-Aldrich). From each lysate, 35 µg of protein were resolved in SDS-PAGE gel at 8% and 15% and membranes of polyvinylidene fluoride (PVDF) (GE Healthcare) were incubated for one night at 4° C. with specific primary antibody: anti-SOD3 (1: 250, Santa Cruz), anti-Phospho-PKAα/β/γ (Thr198, 1: 250, Santa Cruz), anti-NOS2 (1: 250, Santa Cruz), anti-cytochrome C (1: 1000, Calbiochem). Protein expression was normalised and verified through the detection of β-actin (1: 5000; Sigma-Aldrich) and expressed as mean±SD (DD, standard deviation) (% with respect to the control).

Statistical analysis.

At least four independent experiments were conducted for each experimental protocol; the results were expressed as means±SD (SD, standard deviation) of independent experiments conducted on four technical replicates. The one-directional ANOVA followed by the Bonferroni's post hoc tests was used for statistical analysis and the paired differences were compared with the Mann-Whitney's U tests.

Results

A) Cell viability after treatment with vitamin D3 (vitD) and lipoic acid (LA) over time.

In order to evaluate the potential effect of vitD and LA—alone or combined (composition according to the invention)—on the cell viability of the astrocytes, the MTT test was conducted as response to the dose and time. Firstly, the effect depending on the concentration of LA alone (comprised between 10 µM and 100 µM) on the cell viability over 24 hours (starting from 15 minutes to 1440 minutes) was analysed, with the aim of identifying the best concentration to be used. FIG. 1(a) illustrates the time-dependent and dose-response studies (ranging from 10 µM to 100 µM) of LA measured in astrocytes. FIG. 1(b) illustrates the time-dependent and dose-response studies of 50 µM LA combined with 100 nM vitD measured in astrocytes. The data is expressed as means±SD (%) of five independent experiments normalised to the control values (line 0%).

As shown in FIG. 1 (a) 50 µM of LA seems to be the dose capable of inducing greater effect (p<0.05) with respect to the control and at higher concentrations (10, 25, 100 µM, p<0.05) over the entire period of stimulation and the maximum effect of about 66% with respect to the control was observed at 1440 minutes. This concentration of LA was maintained for all subsequent experiments. Thus, further experiments were conducted to study the combination of 50 µM LA and 100 nM vitD (composition according to the invention) on cell viability. As indicated in FIG. 1 (b), vitD increased the cell viability of the astrocytes in a time-dependent fashion with a maximum effect, about 22% (p<0.05) at 1440 min with respect to the control. Furthermore, the combination of LA and vitD (composition according to the invention) was capable of significantly increasing cell viability (p<0.05) over time with respect to the control (p<0.05) and with respect to 50 µM LA and 100 nM vitD alone starting from 60 min of stimulation (p<0.05).

The composition according to the invention exercised greater effect at 1440 min with respect to the control (p<0.05) and with respect to 50 µM LA and 100 nM vitD alone (about 20.5% and 64%, respectively). Thus, this stimulation period was maintained for all the subsequent experiments. This data corroborates the theory of synergic effects exercised by vitD and LA in the astrocytes indicating the potential of the composition of the invention at slowing cerebral aging and thus at treating neurodegenerative diseases.

B) Permeability of vitD and LA through the blood-brain barrier (BBB).

A blood-brain barrier (BBB) permeability study was conducted with the aim of better understanding the capacity of 100 nM vitD and 50 µM LA—alone or combined (composition according to the invention)—to cross the blood-brain barrier over time and thus predict the bioavailability thereof in the brain. FIG. 2 (a) shows the absorption capacity of vitD e LA—alone or combined—through the blood-brain barrier; FIG. 2(b) shows the quantification of vitD and FIG. 2(c) shows the quantification of LA in the basolateral environment of the barrier model. The data is expressed as the mean±SD (%) of five independent experiments normalised to the control values (line 0%).

As indicated in FIG. 2 (a), the basolateral volume analysis showed a time-dependent increase of the absorption capacity caused by 100 nM vitD and 50 µM LA alone with respect to the control (p<0.05) and greater effects were observed at 1440 min (about 49.5% and 40.5%, respectively). The combination of vitD and LA (composition according to the invention) increased the absorption capacity with respect to the control (p<0.05) over time with respect to the single administrations of LA and vitD starting from 60 minutes, as previously observed on cell viability (p<0.05). This data corroborates a cooperative and synergic effect of vitD and LA (composition according to the invention) even during the permeability test.

The subsequent quantifications of vitD and LA were conducted to determine the specific concentration present in the baseline volume of the BBB model. In particular, the absorption of vitD and LA over time depended on time and the combination of VitD and LA (composition according to the invention) revealed to be essential towards amplifying the capacity of the single components to cross the blood-brain barrier. As a matter of fact, the specific quantifications of vitD (FIG. 2 (b)) and LA (FIG. 2 (c)) showed a greater effect of the combination of VitD and LA (composition according to the invention) with respect to the separate administration (about 26% and 63%, respectively), with a maximum effect at 1440 min (p<0.05 vs control). All these results corroborate the theory that the combination of LA and vitD (composition according to the invention) is capable of exercising the beneficial effects directly on the viability of the astrocytes due to their capacity to cross the blood-brain barrier.

C) Analysis of the mitochondrial activity after treatments with LA and vitD in oxidative conditions.

The cell viability, the production of ROS and the mitochondrial potential were evaluated in astrocytes, with the aim of studying the potential action for preventing cell aging in oxidative conditions. FIG. 3(a) illustrates the cell viability, FIG. 3(b) illustrates the production of ROS, FIG. 3(c) illustrates the mitochondrial membrane potential measured on astrocytes treated with vitD and LA—alone or combined—for 24 hours of pre-stimulation with $H_2O_2$. The data is expressed as means±SD (%) of five independent experiments normalised to the control values (line 0%).

Exposure to 200 µM of $H_2O_2$ significantly reduced cell viability by 46% with respect to the control; on the contrary, after the post-treatment with 50 µM LA and 100 nM vitD—alone or combined (composition according to the invention)—cell viability increased significantly. Greater effect was obtained with the combination of LA and vitD (composition according to the invention) which restored the cell loss (FIG. 3 (a)).

Given that the main theory on which cerebral aging is based regards the oxidative condition, further experiments on the production of ROS were conducted. 50 µM LA, 100 nM vitD and the combination of both (composition according to the invention) were capable of maintaining the production of ROS below the physiological level (p>0.05 vs control), corroborating the theory of the safety thereof in use (FIG. 3 (b)). Exposure of the astrocytes to 200 µM of $H_2O$ significantly increased the production of intracellular ROS as illustrated in FIG. 3 (b) by about 30% with respect to the control (p<0.05); post-treatment with 50 µM LA and 100 nM vitD alone significantly reduced the production of ROS (about 43% and 57%, respectively, with respect to $H_2O_2$ alone) and the simultaneous administration of LA and vitD (composition according to the invention) improved the reduction of ROS with respect to 200 µM of $H_2O_2$, 50 µM of LA and 100 nM of vitD alone (p<0.05, about 78%, 62% and 50%, respectively).

Given that the alteration of formation of a protonic gradient through the inner mitochondrial membrane is deemed to be one of the key indicators of cell viability, the mitochondrial potential was analysed. Treatments with 50 µM of LA, 100 nM of vitD and with the combination of both (LA+vitD, composition according to the invention) induced a significant increase of the red fluorescence, corroborating the active role of 50 µM of LA, 100 nM of vitD and the combination thereof on mitochondrial activity (p<0.05). Furthermore, the combination of LA and vitD (composition according to the invention) seems to have greater effect with respect to 50 µM LA and 100 nM vitD alone (about 23% and 60%, respectively). The cells treated with $H_2O_2$ showed variations in the fluorescence signal which lead to a reduced red fluorescence signal and an increased green fluorescence signal, indicating a significant dissipation of the mitochondrial potential and of the cell loss with respect to the control (p<0.05, FIG. 3 (c)). Post-treatment with 50 µM LA, 100 nM vitD alone and with the combination of both (LA+vitD, composition according to the invention) the dissipations of the mitochondrial potential were significantly inverted as shown in FIG. 3 (c) with respect to 200 µM $H_2O_2$ alone (p<0.05). In particular, the combination of LA and vitD suppressed the mitochondrial dissipation effect induced by $H_2O_2$, moving the fluorescence signal from green to red (p<0.05). These results indicate that the combination of LA and vitD (composition according to the invention) can reduce the apoptosis induced by $H_2O_2$ through the mitochondrial-mediated pathway.

D) Study of the intracellular pathways activated by LA and vitD in oxidative conditions.

The dissipation of the mitochondrial potential in oxidative conditions is known to start a cascade of events that lead to the activation of caspases, which trigger apoptosis in turn. In this context, p53, as a key factor involved in aging, in oxidative stress and in neurodegeneration, and cytochrome C, as a key regulator of the cell energy metabolism and of the apoptosis, were studied in the astrocytes.

The data indicated in FIG. 4 (a) showed a reduction of the activity of p53 after stimulation with 50 µM LA and 100 nM vitD alone or combined (p<0.05 vs control), corroborating the previous data on the safety of the combination (composition according to the invention). The activity of p53 increased significantly in the astrocytes treated with $H_2O_2$ (p<0.05 vs control) and the subsequent stimulation with 50 µM LA and 100 nM vitD alone reduced it significantly (p<0.05). Furthermore, the combination of LA and vitD (composition according to the invention) amplified the reduction with respect to 200 µM of $H_2O_2$ by about 80% and with respect to the single administrations by about 69% and 60% respectively (p<0.05), determining conditions favourable to survival.

In order to examine the involvement of the caspase pathways, the expression of cytochrome C was analysed in the same conditions. FIG. 4 (b) and FIG. 5 (part regarding cytochrome C) show results similar to those obtained for p53 under stimulation with 50 µM LA and 100 nM vitD alone, thus confirming the beneficial effects observed previously. Also the combination of LA and vitD (composition according to the invention) maintained the cytochrome Cat baseline level, corroborating the mitochondrial wholeness.

Furthermore, the cells treated with $H_2O_2$ showed an increase in the expression of cytochrome C which was reduced by the subsequent stimulation with 50 µM LA and 100 nM vitD alone or combined (composition according to the invention) (p<0.05).

With the aim of excluding any oxidative damage induced by the stimulations, the expressions of SOD3 and iNOS were studied. As indicated in FIG. 4 (c), in FIG. 4 (d) and in FIG. 5 (parts regarding SOD3 and iNOS), the expressions of SOD3 and iNOS increased significantly in the presence of 200 µM di $H_2O_2$ (p<0.05 vs control), corroborating the theory of the involvement of the oxidative stress in the death of astrocytes. Furthermore, post-stimulation with 50 µM LA and 100 nM vitD alone significantly reduced the expression of SOD3 and iNOS with respect to 200 µM of $H_2O_2$ and a greater reduction was obtained from the combined stimulation with 50 µM LA and 100 nM vitD (composition according to the invention) with respect to 200 µM of $H_2O_2$ ($p<0.05$), indicating a beneficial effect at fighting the aging process.

Given that neuroinflammation is a common cause of cerebral aging, PKA—a key anti-inflammatory marker—was studied in the same conditions (FIG. 4 (e) and FIG. 5 (part regarding PKA)). The expression of PKA observed in the astrocytes showed a significant increase of the presence of 50 µM LA and 100 nM of vitD alone ($p<0.05$) and the combination thereof amplified this effect supporting the anti-inflammatory effect of the combination of LA and vitD (composition according to the invention). In the presence of 200 µM of $H_2O_2$ a significant reduction was observed with respect to the control and the post-stimulation with 50 µM of LA and 100 nM of vitD restored the mechanism ($p<0.05$). The combination of LA and vitD (composition according to the invention) added after 200 µM of $H_2O_2$ had an effect on the expression of PKA similar to the one observed without $H_2O_2$, indicating the capacity of the combination to prevent the induction of the inflammatory cascade under oxidative stress.

It is known that a natural consequence of apoptosis lies in cell loss and the β-amyloid analysis showed the alteration of the cerebral tissue. As indicated in FIG. 4 (f) and in FIG. 5 (part regarding β-actin, abbreviated as β-act), stimulation with 200 µM of $H_2O_2$ caused a significant increase of the level of APP, corroborating the previous data on cell death. Furthermore, post-stimulations with 50 µM LA and 100 nM vitD alone were not capable of reducing the damage, as shown by the reduction of the level of APP ($p<0.05$) with respect to 200 µM of $H_2O_2$. Lastly, the greater effect was observed in the presence of the combined treatment with LA and vitD (composition according to the invention), indicating the effectiveness of the combination during cerebral damage.

To summarise, FIGS. 4(a) and 4(f) show the measurements of the activities of p53 and APP, respectively, measured during the ELISA test; FIGS. 4(b), 4(c), 4(d) and 4(e) show the densiometric analysis of the expressions of cytochrome C, SOD3, iNOS, p-PKA and b-actin, respectively, obtained by analysing the Western blot on whole astrocyte lysates The data is expressed as means±SD (%) of five independent experiments normalised to the control values (line 0%). FIG. 5 shows the Western blot of SOD3, iNOS, p-PKA and 3-actin in astrocytes under oxidative stress.

Furthermore, the ERK/MAPK and PI3K-Akt pathways play a crucial role in the regulation of the neuronal and cerebral survival. FIGS. 6(a) and 6(b) show the quantification of the activities of p-ERK and p-Akt respectively, measured at 24 hours in astrocytes treated with vitD and LA alone and combined in pre-stimulation with $H_2O_2$. The data is expressed as means±SD (%) of five biological replicates normalised for control values (line 0%). 50 µM LA and 100 nM vitD alone confirmed their capacity to increase cell viability, activating ERK and Akt mediators, as indicated in FIGS. 6 (a) and 6(b). The combination of LA with vitD (composition according to the invention) amplifies the activation of kinase with respect to the control and to the single administrations ($p<0.05$). Exposure to 200 µM of $H_2O_2$ significantly reduced the activities of ERK and Akt by about 6% and 7% with respect to the control, respectively; on the contrary, the subsequent post-treatment with 50 µM LA and 100 nM vitD—alone or combined—nullified the effects observed previously indicating the activation of survival pathways. Furthermore, the combination of LA with vitD (composition according to the invention) showed greater effect in the activity of PI3/Akt with respect to ERK/MAPK, corroborating the theory that all neuronal survival signals were activated after the activation of Akt.

E) Evaluation of LA and activity of vitD under accumulation of iron.

Figure 7:
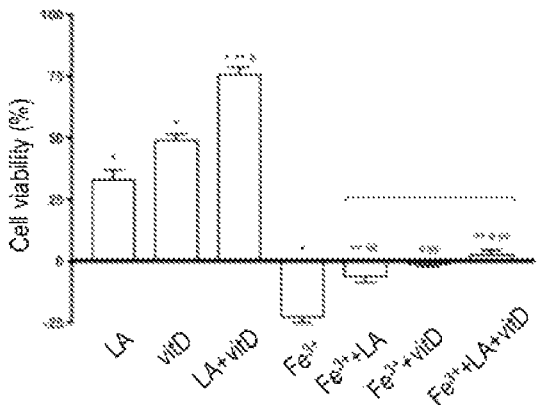
FIGS. 7(a), (b) and (c): cell viability, production of ROS and quantification of the iron in the astrocytes pre-treated with $Fe^{3+}$.
Figure 7:
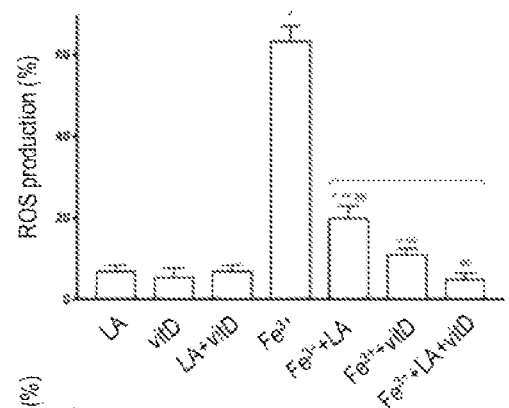
Figure 7:
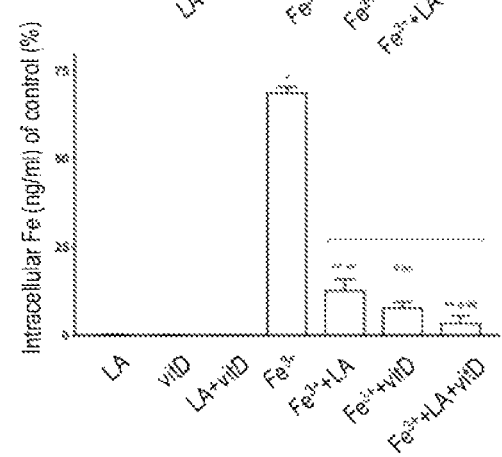

Iron can be progressively accumulated in the brain during normal aging; it can be preserved at abnormal accumulations in neurodegenerative disorders. Given that LA is a potent chelator of divalent metal ions and vitD is capable of preventing the damage induced by the accumulation, further experiments were conducted on the astrocytes to verify their protective capacity in the brain. Thus, cell viability and production of ROS were evaluated in astrocytes after 6 days of stimulation, as indicated in FIGS. 7 (a), (b). In particular, FIG. 7(a) shows the cell viability, FIG. 7(b) shows the production of ROS and FIG. 7(c) shows the quantification of intracellular iron measured on astrocytes pre-treated with $Fe^{3+}$. The data is expressed as means±SD (%) of five independent experiments normalised to the control values (line 0%).

Exposure to 300 µM $Fe^{3+}$ significantly reduced cell viability by about 23% with respect to the control ($p<0.05$); vice versa, after post-treatment for another 6 days with 50 µM LA and 100 nM vitD alone, cell viability leads to control values, confirming the iron chelation and damage repair ($p>0.05$) capacity thereof. Furthermore, the simultaneous stimulation with LA and vitD (composition according to the invention) was capable of amplifying the beneficial effect exercised by the single administration ($p<0.05$), corroborating the idea of its potential to reduce cerebral damage.

Further experiments on the production of ROS were conducted to study the role played by oxidation in the presence of accumulation of iron. Exposure of astrocytes to 300 µM of $Fe^{3+}$ for 6 days significantly increased the production of intracellular ROS, as illustrated in FIG. 7 (b) about 60% with respect to the control ($p<0.05$). Furthermore, post-treatment for another 6 days with 50 µM LA and 100 nM vitD alone significantly reduced the production of ROS (about 68% and 83%, respectively, with respect to $Fe^{3+}$ alone) and the simultaneous administration of LA and vitD (composition according to the invention) improved the reduction of ROS with respect to 300 µM $Fe^{3+}$ by about 92%. These results indicate the capacity of the composition according to the invention to fight the oxidative condition caused by accumulation of iron.

Given that the accumulation of iron is a major cause of cerebral damage, it is essential to find strategies for preventing it; thus, some experiments were conducted with the aim of evaluating the amount of iron that remains in the cells. As indicated in FIG. 7 (c), 300 µM $Fe^{3+}$ increased the intracellular accumulation after 6 days of stimulation by about 69% with respect to the control ($p<0.05$), indicating that 6 with an excess of iron was a condition sufficient to create damage in the astrocytes. Post-stimulation for another 6 days with 50 µM LA and 100 nM vitD alone significantly reduced the accumulation of iron (about 81% and 88%, respectively against $Fe^{3+}$ alone) and the simultaneous administration of LA and vitD (composition according to the invention) improved the prevention of the accumulation with respect to 300 µM $Fe^{3+}$ by about 95% and with respect to single administration ($p<0.05$). These results indicate the capacity of the composition according to the invention to fight the iron-dependent damage, preventing the accumulation thereof.

Furthermore, to confirm the protection exercised by LA and vitD, the activity of p53 was analysed too.

As shown in FIG. 8 (a), the administration of 300 μM $Fe^{3+}$ for 6 days caused a considerable increase of the activity p53 ($p<0.05$) with respect to the control, corroborating the previous observations on cell viability. Post-stimulation with 50 μM LA and 100 nM vitD alone for another 6 days was capable of reducing the activation of p53 ($p<0.05$ vs control) by about 84% and 88%, respectively, with respect to 300 μM $Fe^{3+}$. Lastly, the combined effect of LA with vitD (composition according to the invention) for another 6 days after 300 μM of $Fe^{3+}$ was capable of amplifying the reduction of the activity of p53 ($p<0.05$) with respect to 300 μM of $Fe^{3+}$ (about 93%) and with respect to the single administrations ($p<0.05$), corroborating the beneficial effects observed previously.

The production, the accumulation and aggregation of APP during neurodegeneration are influenced by a number of modulators and the latter including iron, hence the level of APP was also detected in these conditions. As illustrated in FIG. 8 (b), exposure of astrocytes to 300 μM of $Fe^{3+}$ for 6 days significantly increased the level of APP by about 43% with respect to the control ($p<0.05$); post-treatment for another 6 days with 50 μM LA and 100 nM vitD alone significantly reduced the level of APP (about 63% and 55%, respectively against 300 μM $Fe^{3+}$) and the simultaneous administration of LA and vitD (composition according to the invention) amplified reduction with respect to 300 μM $Fe^{3+}$ and with respect to 50 μM LA and 100 nM vitD alone ($p<0.05$, about 82%, 53% and 61%, respectively). These results confirm the effectiveness of the composition according to the invention at preventing the iron-dependent damage in the brain.

Cell oxidative stress and antioxidant enzymatic deregulation are linked to aging-related cerebral degeneration, hence the expression of SOD3 was studied in the same conditions indicated previously. Stimulation for 6 days with $Fe^{3+}$ 300 μM caused a significant increase of the expression of SOD3 ($p<0.05$) with respect to the control which was reduced by subsequent stimulation for 6 more days with 50 μM LA or 100 nM vitD alone ($p<0.05$), indicating a positive effect of 50 μM LA and 100 nM vitD to maintain a correct balance of the oxidising effect in astrocytes (FIG. 8 (c)). Furthermore, the combined effect of LA with vitD (composition according to the invention) added for 6 days after 300 μM $Fe^{3+}$ was capable of significantly reducing the expression of SOD3 ($p<0.05$) with respect to 300 μM of $Fe^{3+}$ (about 78%) and with respect to 50 μM of LA and 100 nM vitD alone (about 67% and 40% respectively). This data allows to exclude the presence of oxidative damage and the activation of the inflammatory cascade in the presence of accumulation of iron, corroborating the theory that the composition according to the invention is effective at treating diseases, symptoms or disorders associated with cerebral aging, in particular at treating neurodegenerative diseases.

Lastly, the ERK/MAPK activity was studied with the aim of proving that combined stimulation with LA and vitD could prevent the loss and damage of iron-dependent cells, thus activating a rescue mechanism such as the survival pathways. Exposing the astrocytes to 300 μM $Fe^{3+}$ for 6 days regulated the activation of ERK/MAPK as indicated in FIG. 8 (d) ($p<0.05$ vs control), indicating a negative effect and suggesting that the generation of iron-dependent ROS activates this pathway; post-stimulation for another 6 days with 50 μM LA and 100 nM vitD alone showed a significant reduction with respect to 300 μM $Fe^{3+}$ ($p<0.05$), corroborating the beneficial effects observed previously. Furthermore, the simultaneous administration of LA and vitD (composition according to the invention) made the observed reduction of over-expression more marked with respect to 300 μM $Fe^{3+}$ ($p<0.05$), confirming the observation of a better survival of the astrocytes after the damage.

To summarise, FIGS. 8(a), 8(b) and 8(d) show the measurements of the activities of p53, APP and ERK/MAPK, respectively conducted using the ELISA test. The data is expressed as means±SD (%) of five independent experiments normalised to the control values (line 0%). FIGS. 8(c') and 8(c") show the densiometric and Western blot analysis of the SOD3 expression of the cytochrome obtained in astrocyte lysates. The data is expressed as means±SD (%) of five normalised and verified independent experiments on the detection of b-actin.

Discussion of the Results

The experimental results outlined above show that the combination of lipoic acid (LA) and D3 (vitD) exercises a synergic and cooperative effect in the treatment of astrocytes in oxidative stress conditions indicating the potential effectiveness of the composition of the invention at treating diseases, symptoms and/or disorders associated with cerebral aging, in particular at treating neurodegenerative diseases, and at the non-therapeutic treatment for the slowing down of aging and disorders associated with aging. Furthermore, the combined treatment with LA and vitD according to the invention improved the negative effects of pre-neurodegenerative conditions.

The combination of LA and vitD is capable of producing beneficial effects directly on the viability of astrocytes, given that these substances are capable of crossing the blood-brain barrier. Furthermore, the combination of LA and vitD increases the absorption rate of the two substances with respect to the control over time and with respect to the single administration starting from 60 minutes, corroborating the cooperative effects of LA and vitD even during permeability.

Given that the main theory on which cerebral aging is based regards the oxidative stress condition, the following experiments on the production of ROS were conducted. In oxidative conditions, the combined treatment with LA and vitD according to the invention improves the reduction of the level of ROS.

The alteration of the formation of a protonic gradient through the inner mitochondrial membrane is considered one of the key indicators of cell; the combination of LA and vitD according to the invention suppressed the effect of mitochondrial dissipation induced by $H_2O_2$ proving the capacity thereof to reduce the apoptosis induced by $H_2O_2$ through the pathways by means of mitochondria.

The intracellular pathways activated by LA and vitD during the oxidative condition were studied. The results indicated above suggest a reduction of the activity of p53 after stimulation with LA and vitD which is correlated to conditions favourable for cell survival. Furthermore, the involvement of the caspase pathway was examined by analysing the expression of cytochrome C. The combination of LA and vitD according to the invention is capable of reducing the expression of cytochrome C during oxidative damage, supporting the mitochondrial wholeness. Furthermore, it was proven that stimulation with LA and vitD in oxidative conditions can reduce the death cell and increase cell survival, through the activation of the ERK and Akt mediators. Even the main pathways involved in oxidative stress (SOD3 and iNOS) are inhibited by the administration of LA and vitD, indicating a better cell survival.

Given that neuroinflammation is a common cause of cerebral aging, PKA—a key anti-inflammatory marker—was also studied at the same conditions. The expression of PKA observed in astrocytes showed a significant increase in the presence of LA and vitD and the combination thereof according to the invention amplified this effect, corroborating the theory of an anti-inflammatory activity of the composition according to the invention.

The combination of LA and vitD according to the invention added after $H_2O_2$ had a similar effect on the expression of PKA. This result also allows to exclude the involvement of the inflammation cascade during the treatment with the combination of LA and vitD.

Furthermore, it was proven that exposure to $Fe^{3+}$ significantly reduces cell viability and the increase of production of ROS and that the combination of LA and vitD according to the invention can prevent the damage dependent on $Fe^{3+}$ in astrocytes. Post-treatment with LA and vitD was capable of repairing the damage caused by accumulation of iron. Furthermore, it was proven that the combination of LA and vitD according to the invention is capable of preventing the intracellular iron accumulation-related damage due to the capacity thereof to prevent the deposit of iron facilitating the elimination thereof. Furthermore, even though the presence of iron caused a harmful condition for the cells, the response to the treatment significantly activated the cell survival mechanisms (ERK) deactivating the apoptosis mechanisms (p53). Lastly, it was proven that these effects are mediated by the inhibitor effect of LA on the oxidative (SOD3) and inflammatory (APP) system.

BIBLIOGRAPHY

1. Z. Jovanovic, "Antioxidative defense mechanisms in the aging brain", Archives of Biological Sciences, vol. 66, no. 1, pp. 245-252, 2014.
2. D. Harman, "The biologic clock: the mitochondria?", Journal of the American Geriatrics Society, vol. 20, no. 4, pp. 145-7, 1972.
3. J. Nordberg, E. S. Arner, "Reactive oxygen species, antioxidants, and the mammalian thioredoxin system", Free Radical Biology and Medicine, vol. 31, no. 11, pp. 1287-312, 2001.
4. R. J. Ward, F. A. Zucca, J. H. Duyn et al., "The role of iron in brain aging and neurodegenerative disorders", Lancet Neurol, vol. 13, no. 10, pp. 1045-60, 2014
5. F. Uberti, V. Morsanuto, C. Bardelli et al., "Protective effects of 1α,25-Dihydroxyvitamin D3 on cultured neural cells exposed to catalytic iron", Physiological Report, vol. 4, no. 11, pii: e12769, 2016.
6. S. Schildge, C. Bohrer, K. Beck et al., "Isolation and culture of mouse cortical astrocytes", Journal of Visualized Experiments, no. 71, pii: 50079, 2013.
7. I. Emanuelsson, M. Almokhtar, K. Wikvall et al., "Expression and regulation of CYP17A1 and 313-hydroxysteroid dehydrogenase in cells of the nervous system: Potential effects of vitamin D on brain steroidogenesis", Neurochemistry International, vol. 113, pp. 46-55, 2017.
8. L. LO, J. Li, Y. Zhu et al., "$H_2O_2$-induced changes in astrocytic cultures from control and rapidly aging strains of mouse", International Journal of Neuroscience, vol. 118, no. 9, pp. 1239-50, 2008.
9. J. Park, D. G. Lee, B. Kim et al., "Iron overload triggers mitochondrial fragmentation via calcineurin-sensitive signals in HT-22 hippocampal neuron cells", Toxicology, vol. 337, pp. 39-46, 2015.
10. F. Uberti, V. Morsanuto, S. Ghirlanda et al., "Iron Absorption from Three Commercially Available Supplements in Gastrointestinal Cell Lines", Nutrients, vol. 9, no. 9, pii: E1008, 2017.
11. Y. A. Zorkina, N. E. Volgina, G. E. Gorlachev et al., "Effect of γ-irradiation on expression of tight and adherens junction protein mRNA on in vitro blood-brain barrier model", Bulletin of Experimental Biology and Medicine, vol. 158, no. 1, pp. 127-36, 2014.
12. C. Kulczara, K. E. Lubina, S. Lefebvrea et al., "Development of a direct contact astrocyte-human cerebral microvessel endothelial cells blood—brain barrier coculture model", Journal of Pharmacy and Pharmacology, vol. 69, no. 12, pp. 1684-1696, 2017.
13. P. P. Goti, J. J. Saysani, P. B. Patel, "Spectrophotometric method development and validation for estimation of α-Lipoic acid in tablet dosage form", International Journal of Pharmacy and Pharmaceutical Sciences, vol. 4, pp. 519-522, 2012.
14. F. Uberti, C. Bardelli, V. Morsanuto et al., "Stimulation of the Non neuronal Cholinergic System by Highly Diluted Acetylcholine in Keratinocytes", Cells Tissues Organs, vol. 203, no. 4, pp. 215-230, 2017.
15. F. Uberti, V. Morsanuto, S. Aprile et al., "Biological effects of combined resveratrol and vitamin D3 on ovarian tissue", Journal of Ovarian Research, vol. 10, no. 1, p. 61, 2017.

The invention claimed is:

1. A method for reducing oxidative stress in an astrocyte, comprising administering to the astrocyte a composition comprising a mixture of:
   (I) lipoic acid or a derivative thereof, or an acceptable pharmaceutical salt of lipoic acid or a derivative thereof;
   (II) a vitamin of group D or a derivative thereof, wherein said (II) vitamin of group D is selected from among: vitamin D3 or a derivative thereof, vitamin D2 or a derivative thereof and a mixture thereof; wherein:
   (a) the lipoic acid or a derivative thereof is 98% to 99.9% of the mixture by weight, and
   (b) the vitamin D3 and/or vitamin D2, or a derivative thereof, is 0.001% to 1% 0.001% to 10% of the mixture by weight and, optionally, said composition comprises at least one pharmaceutical additive and/or excipient.

2. The method of claim 1, wherein said (II) vitamin of group D is a vitamin D3 or a derivative thereof.

3. The method of claim 1, wherein said (II) vitamin of group D is a vitamin D2 or a derivative thereof.

4. The method of claim 1, wherein said (II) vitamin of group D is a mixture of vitamin D3 or a derivative thereof, and of vitamin D2, or a derivative thereof.

5. The method of claim 4, wherein said mixture of vitamin D3 or a derivative thereof and of vitamin D2 or a derivative thereof is in a vitamin D3:vitamin D2 by weight ratio comprised in the range from 10:1 to 1:10.

6. The method of claim 1, wherein said (I) lipoic acid is a racemic form of lipoic acid or acceptable pharmaceutical or food grade salt thereof or a derivative thereof.

* * * * *